United States Patent [19]

Ackermann

[11] Patent Number: 4,822,806
[45] Date of Patent: Apr. 18, 1989

[54] α-METHYL-(6-PHENOXY)-2-PICOLYL CYCLOPROPANECARABOXYLATES HAVING PESTICIDAL ACTIVITY

[75] Inventor: Peter Ackermann, Pfeffingen, Switzerland

[73] Assignee: Ciba-Geigy Corporation, Ardsley, N.Y.

[21] Appl. No.: 2,370

[22] Filed: Jan. 12, 1987

Related U.S. Application Data

[62] Division of Ser. No. 688,123, Dec. 31, 1984, Pat. No. 4,661,497.

[30] Foreign Application Priority Data

Jan. 12, 1984 [CH] Switzerland .............. 140/84
Nov. 30, 1984 [CH] Switzerland ............. 5713/84

[51] Int. Cl.$^4$ .............. C07D 213/64; A01N 43/40
[52] U.S. Cl. .............. 514/345; 514/351; 546/300; 546/301; 546/302
[58] Field of Search .............. 546/300, 301, 302; 514/345, 351

[56] References Cited

U.S. PATENT DOCUMENTS 4,172,135 10/1979 Kristiansen et al. ............ 514/345
4,221,799 9/1980 Van Heertum et al. .......... 514/345
4,491,585 1/1985 Fuchs et al. .................... 514/345

FOREIGN PATENT DOCUMENTS 59-152303 8/1984 Japan ........................... 546/302

OTHER PUBLICATIONS

Agri. Bio. Chem., 40(1), 247-249, (1976) Matsuo et al.
Quarterly Review, Synthetic Pyrethroids-a New Class of Insecticide-Elliot et al., pp. 473-505.

Primary Examiner—Alan L. Rotman
Attorney, Agent, or Firm—Kevin T. Mansfield; Edward McC. Roberts

[57] ABSTRACT

The invention relates to α-methyl-(6-phenoxy)-2-picolyl cyclopropanecarboxylates of the formula

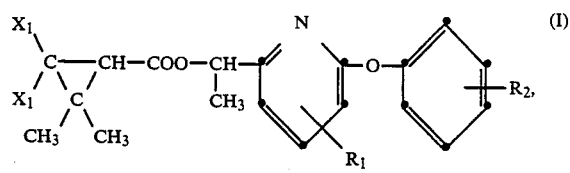

wherein
$X_1$ is methyl or halogen,
$R_1$ is hydrogen or halogen, and
$R_2$ is hydrogen, halogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, $C_1$-$C_4$haloalkylthio, $C_2$-$C_4$alkenyl, $C_2$-$C_4$alkynyl, nitro or cyano.

The invention also relates to the preparation of these esters and to the use thereof in pest control.

3 Claims, No Drawings

α-METHYL-(6-PHENOXY)-2-PICOLYL CYCLOPROPANECARABOXYLATES HAVING PESTICIDAL ACTIVITY

This is a division of application Ser. No. 688,123, filed on Dec. 31, 1984, now U.S. Pat. No. 4,661,497 issued Apr. 28, 1987.

The present invention relates to α-methyl-(6-phenoxy)-2-picolyl cyclopropanecarboxylates, to the preparation of these esters and to the use thereof in pest control.

The α-methyl-(6-phenoxy)-2-picolyl cyclopropanecarboxylates have the formula

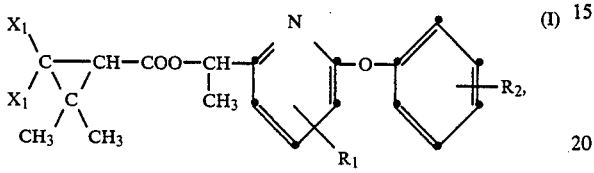

wherein
$X_1$ is methyl or halogen,
$R_1$ is hydrogen or halogen, and
$R_2$ is hydrogen, halogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, $C_1$-$C_1$haloalkylthio, $C_2$-$C_4$-alkenyl, $C_2$-$C_4$alkynyl, nitro or cyano.

Halogen in the above definition is fluorine, chlorine, bromine or iodine.

The alkyl, alkoxy, alkylthio, haloalkyl, haloalkoxy, haloalkylthio, alkenyl and alkynyl groups may be straight chain or branched. Examples of such groups comprise methyl, methoxy, methylthio, trifluoromethyl, trifluoromethoxy, ethyl, ethoxy, propyl, isopropyl, n-butyl, vinyl, 1-propenyl, ethynyl, 1-propynyl.

Particularly preferred compounds of formula I are those wherein
$X_1$ is methyl or chlorine,
$R_1$ is hydrogen or halogen, and
$R_2$ is hydrogen, halogen, $C_1$-$C_4$alkyl, $C_1$-$C_4$alkoxy, $C_1$-$C_4$alkylthio, vinyl or ethynyl.

The most preferred compounds of formula I are those wherein
$X_1$ is methyl or chlorine,
$R_1$ is hydrogen, and
$R_2$ is hydrogen or halogen.

The compounds of formula I are prepared by methods whih are known per se, e.g. as follows:

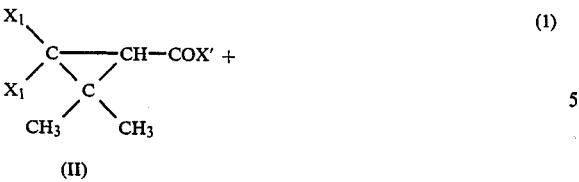

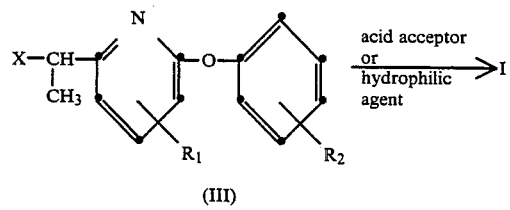

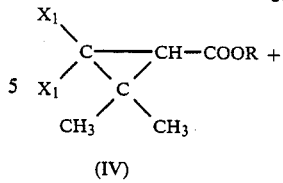

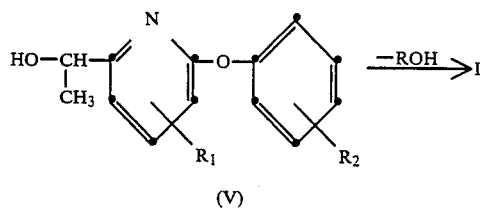

In formulae II to V, $R_1$, $R_2$ and $X_1$ are as defined for formula I.

In formulae II and III, one of X and X' is a hydroxyl group and the other is a halogen atom, preferably chlorine or bromine, or both X and X' are a hydroxyl group, and in formula IV, R is $C_1$-$C_4$alkyl, preferably methyl or ethyl. Suitable acid acceptors are in particular tertiary amines, such as trialkylamine and pyridine, and also hydroxides, oxides, carbonates and bicarbonates of alkali metals and alkaline earth metals, and in addition alkali metal alcoholates, for example potassium tert-butylate and sodium methylate. As hydrophilic agent, it is possible to use e.g. dicyclohexylcarbodiimide. Processes 1 and 2 are carried out at a reaction temperature in the range from −10° to 120° C., usually from 20° to 80° C., under normal or elevated pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxamides; aliphatic, aromatic and halogenated hydrocarbons, especially benzene, toluene, xylenes, chloroform and chlorobenzene; nitriles, such as acetonitrile; dimethyl sulfoxide; and ketones, such as acetone and methyl ethyl ketone.

The starting materials of formulae II to V are known or can be prepared by methods analogous to known ones.

The compounds of formula I are obtained in the form of a mixture of different optically active isomers if inhomogeneous optically active starting materials are used in the reaction. The different mixtures of isomers can be separated into the individual isomers by known methods. A compound of formula I is to be understood as comprising the individual isomers and the mixtures thereof.

The compounds of formula I are suitable for controlling a variety of animal and plant pests. The compounds of formula I can thus be used for controlling insects, for example of the orders: Lepidoptera, Coleoptera, Homopterea, Heteroptera, Diptera, Thysanoptera, Orthoptera, Anoplura, Siphonaptera, Mallophaga, Thysanura, Isoptera, Psocoptera and Hymenoptera and mites and ticks of the order Acarina.

The compounds of formula I are particularly suitable for controlling plant-destructive insects, especially plant-destructive feeding insects, in ornamentals and crops of useful plants, in particular in cotton and rice crops (e.g. *Spodoptera littoralis, Heliothis virsescens, Nephotettix cincticeps, Nilaparvata lugens, Chilo suppressalis* and *Laodelphax striatellus*) and in vegetable and fruit crops (e.g. *Leptinotarsa decemlineata, Myzus persicae, Laspeyresia pomonella* and *Adoxophyes reticulana*), and for controlling soil insects (e.g. *Aulacophora femoralis, Chortophila brassicae, Diabrotica balteata, Pachnoda savignyi* and *Scotia ypsilon*).

The compounds of formula I are also very effective against flies, e.g. Musca domestica and mosquito larvae, and against ectoparasitic mites and ticks, e.g. of the families Ixodidae, Argasidae and Dermanyssidae. In addition, the compounds of formula I have broad ovicidal and ovolarvicidal activity.

The compounds of formula I also have excellent activity against insects that feed on keratin such as Lepidoptera larvae, e.g. Tineola spec. and Tinea spec., and also Coleoptera larvae, e.g. Anthrenus spec. and Attagenus spec. The compounds of formula I are most suitable for protecting keratinuous material against feeding damage by insects, especially for providing such material with a washfast and lightfast protective finish against insects, in particular moths and beetles. The keratinuous material to be proctected can be both in the raw and in the processed state, for example raw or processed sheep's wool or products made of other animal hairs, hides, furs and feathers.

A particularly important feature is the effectiveness of the compounds of formula I against the larvae of the webbing clothes moth (*Tineola bisselliela*) and the common clothes moth (*Tinea pelionella*) as well as against the larvae of fur beetles and carpet beetles (Attagenus spec. and Anthrenus spec. respectively). The compounds of formula I are thus preferred on the one hand for protecting woollen textiles, for example blankets, wool carpets, woollen underwear, woollen clothing, knits and wool-containing textiles such as blends, one component of which is wool, for example blends of wool and other natural fibers, preferably cotton, and, on the other hand, for protecting furs and hides from attack by the above-mentioned pests.

The acaricidal and/or insecticidal action can be substantially broadened and adapted to prevailing circumstances by addition of other insecticides and/or acaricides. Examples of suitable adddititives include: organophosphorus compounds, nitrophenols and derivatives thereof, formamidines, ureas, other pyrethroids, carbamates, and chlorinated hydrocarbons.

Compounds of formula I are also combined with particular advantage with substances which exert a synergistic or potentiating effect on pyrethroids. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S,-tributylphosphorotrithioate, 1,2-methylenedioxy-4-(2-(octylsulfinyl)propyl)benzene.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of formula I and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid group and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979, and Dr. Helmut Stache: "Tensid Taschenbush", Carl Hanser Verlag, Munich/Vienna, 1981.

The pesticidal compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients for obtaining special effects.

Formulation Examples for liquid active ingredients of formula I (throughout, percentages are by weight)

| 1. Emulsifiable concentrates | (a) | (b) | (c) |
|---|---|---|---|
| compound of formula I | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsion of any required concentration can be produced from such concentrates by dilution with water.

| 2. Solutions | (a) | (b) | (c) | (d) |
|---|---|---|---|---|
| compound of formula I | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| compound of formula I | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for solid active ingredients of formula I (throughout, percentages are by weight)

| 5. Wettable powders | (a) | (b) | (c) |
|---|---|---|---|
| compound of formula I | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| compound of formula I | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
|---|---|---|
| compound of formula I | 5% | 8% |
| talcum | 95% | — |

-continued

| 7. Dusts | (a) | (b) |
|---|---|---|
| kaolin | — | 92% |

Ready for use dusts are obtained by mixing the active ingredient with the carriers, and grinding the mixture in a suitable mill.

| 8. Extruder granulate | |
|---|---|
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granulate | |
|---|---|
| compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrate | |
|---|---|
| compound of formula I | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| siliconeoil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water

EXAMPLE 1

Preparation of the compound of the formula

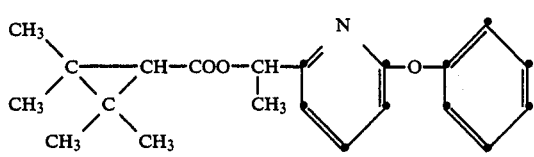

4.3 g of pyridine and 8.9 g of the compound of the formula

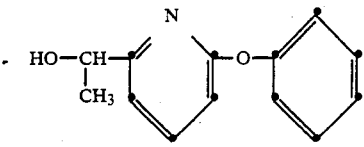

in 35 ml of toluene are added dropwise in succession at 0° C. to 6.7 g of the compound of the formula

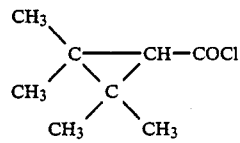

in 30 ml of toluene. The reaction mixture is stirred for 30 hours at 25° C. and then poured into 2N hydrochloric acid and extracted with ether. The ethereal phase is washed with a saturated solution of sodium bicarbonate and a saturated solution of sodium chloride, dried over magnesium sulfate and concentrated. The product is chromatographed through silica gel eluted with toluene/ethyl acetate (95:5), affording the title compound (1) as a mixture of diastereoisomers with a melting point of 63°–64° C.

The following compounds can also be prepared in analogous manner:

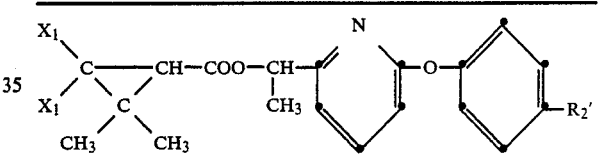

| Comp. | $X_1$ | $R_2'$ | Physical data |
|---|---|---|---|
| 2 | CH$_3$ | Cl | m.p.: 100–101° C. |
| 3 | Cl | Cl | $n_D^{20°}$ = 1.5575 |
| 4 | CH$_3$ | Br | m.p.: 87–88° C. |
| 5 | Cl | Br | $n_D^{20°}$ = 1.5686 |
| 6 | CH$_3$ | J | $n_D^{21°}$ = 1.5609 |
| 7 | Cl | J | $n_D^{20°}$ = 1.5872 |
| 8 | CH$_3$ | F | m.p.: 96° C. |
| 9 | Cl | F | m.p.: 73° C. |
| 10 | CH$_3$ | CH$_3$ | m.p.: 94–96° C. |
| 11 | CH$_3$ | OCH$_3$ | m.p.: 73–75° C. |
| 12 | Cl | SCH$_3$ | $n_D^{27°}$ = 1.5749 |
| 13 | CH$_3$ | SCH$_3$ | m.p.: 52–54° C. |
| 14 | Cl | OCH$_3$ | m.p.: 68–74° C. |
| 15 | CH$_3$ | —CH=CH$_2$ | m.p.: 50–52° C. |
| 16 | CH$_3$ | —C≡CH | m.p.: 73–74° C. |
| 17 | CH$_3$ | H | $[\alpha]_D$ = −41° (C = 0.33;CHCl$_3$) |
| 18 | CH$_3$ | H | $[\alpha]_D$ = +34.5° (C = 0.28;CHCl$_3$) |

EXAMPLE 2

Insecticidal stomach poison action: *Nilaparvata lugens*

Rice plants are sprayed with a solution containing 50 or 100 ppm of test compound.

After the spray coating has dried, the plants are populated with nymphs of *Nilaparvata lugens* in the N$_3$ stage. Two plants are used per test compound and per test species. Evaluation of the mortality rate is made 6 days later. The test is carried out at 22° C. and 60% relative humidity. In this test, the compounds of Example 1 are 100% effective against nymphs of *Nilaparvata lugens* at a concentration of 50 ppm.

EXAMPLE 3

Action against *Diabrotica balteata*

750 ml of sandy soil are mixed with 150 ml of a solution containing 3, 0.75, 0.2 or 0.05 ppm of test compound. Maize seedlings are put into plastic pots filled with the treated soil (4 seedlings per pot, each pot having a diameter of 10 cm). Immediately afterwards, the pots are infested with 10 *Diabrotica balteata* larvae in the $L_3$ stage. Evaluation is made 10 days after infestation with the larvae.

In this test, the compounds of Example 1 are 100% effective against *Diabrotica blateata* larvae in the $L_3$ stage at a concentration of 3 ppm.

EXAMPLE 4

Action against ticks (A) *Amblyomma hebraeum*

50 nymphs are counted into a test tube and immersed for 1 to 2 minutes in 2 ml of an aqueous emulsion prepared from a dilution series containing 10, 1 or 0.1 ppm of test compound. The test tube is then sealed with a standard cotton wool plug and placed on its head to enable the cotton wool to absorb the emulsion. Evaluation is made 1 week later. Each test is repeated twice.

(B) *Boophilus microplus* (larvae)

Tests are carried out with 20 OP-sensitive and 20 OP-resistant larvae using a dilution series similar to that used in Test A. (The resistance refers to the tolerance towards diazinone). Compounds of Example 1 are 100% effective against nymphs and larvae of the ticks *Ambylomma hebraeum* and *Boophilus microplus* at a concentration of 0.1 ppm.

EXAMPLE 5

Insecticidal stomach poison action: *Spodoptera littoralis*

Cotton plants are sprayed with a solution containing 100, 200 or 400 ppm of test compound. After the spray has dried, the plants are populated with *Spodoptera littoralis* larvae in the $L_1$ stage. Two plants are used per test compound and per species. Evaluation of the mortality rate is made after 2, 4, 24 and 48 hours. The test is carried out at 28° C. and 60% relative humidity. In this test, compounds of Example 1 are 100% effective against *Spodopterea littoralis* larvae at a concentration of 400 ppm.

EXAMPLE 6

Action against the webbing clothes moth, the fur beetle and the carpet beetle (a) Exhaust method A 0.4% stock solution of each of the compounds of Example 1 in methyl cellosolve is prepared. Then an aqueous treatment bath containing, in 120 ml of distilled water, 0.12 ml of Sandozin KB ®, 0.6 ml of formic acid 1:10 and 0.75 ml of the respective 0.4% stock solution is prepared at room temperature. Then 3 g of wool flannel are wetted with hot water and put into the bath at room temperature. While constantly circulating the wool sample, the bath temperature is raised to 60° C. in the course of 20 minutes and treatment is carried out for 30 minutes at 60° C. The bath is then cooled, the wool sample rinsed twice for 3 minutes with distilled water, squeezed out by hand and dried in the air. The active ingredient concentration is 1000 ppm, based on the weight of the wool.

The dried sample is subjected to the moth-proofing test (protection against feeding damage caused by the webbing clothes moth *Tineola biselliella* Hum.) and to the resistance test against larvae of the fur beetle (*Attagenus piceus*) and carpet beetle (*Anthrenus vorax Waterhouse*).

Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test samples and, on the other, according to the number of still living organisms.

The tested compound of Example 1 are 100% effective against all three pests.

(b) Pad method

A 0.4% stock solution in methyl cellosolve of each of the compounds of Example 1 is prepared. Each stock solution (12.5 ml) is diluted to 50 ml (solution 1) with methyl cellosolve which contains 0.65 g/l of Sandozin KB ®. Solution 1 (25 ml) is diluted to 50 ml (solution 2) with methyl cellosolve which contains 0.5 g/l of Sandozin KB ®. Solution 2 (25 ml) is then diluted in turn to 50 ml (solution 3) with methyl cellosolve which contains 0.5 g/l of Sandozin KB ®.

3 ml of each of solutions 1, 2 and 3 are poured into crystallisation dishes and a disc of wool flannel is wetted for 3 seconds therein. The moist discs are then padded between aluminium sheets to a pick-up of 50% of each solution. The active ingredient concentrations are, respectively, 500 ppm, 250 ppm and 125 ppm for the discs treated with solutions 1, 2 and 3. The moist discs are then dried in the air and subjected to the same biological tests as described in Example 6a.

The tested compounds of Example 1 are 100% effective against all three pests, even at the lowest concentration of 125 ppm.

What is claimed is:

1. The compound of the formula

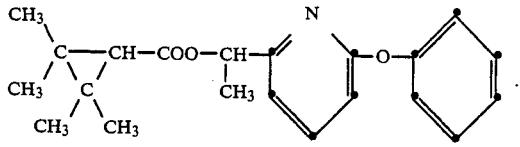

2. A pesticidal composition which comprises, as active ingredient, 0.1 to 99% of the compound according to claim 1, in combination with adjuvants conventionally employed in the art of formulation.

3. A method of controlling a variety of pests of animals and plants and soil pests, which comprises contacting said pests or their habitat with a pesticidally effective amount of the compound of claim 1.

* * * * *